US009668984B2

(12) United States Patent
Giuliani et al.

(10) Patent No.: US 9,668,984 B2
(45) Date of Patent: *Jun. 6, 2017

(54) USE OF COMPOUNDS TO INHIBIT 5 α-REDUCTASE ENZYME ACTIVITY, AND PHARMACEUTICAL AND COSMETIC COMPOSTIONS CONTAINING THEM

(75) Inventors: Giammaria Giuliani, Milan (IT); Anna Benedusi, Milan (IT); Sergio Baroni, Villa d'Adda (IT)

(73) Assignee: GIULIANI S.P.A., Milan (IT)

( * ) Notice: Subject to any disclaimer, the term of this patent is extended or adjusted under 35 U.S.C. 154(b) by 1720 days.

This patent is subject to a terminal disclaimer.

(21) Appl. No.: 13/128,394

(22) PCT Filed: Nov. 10, 2009

(86) PCT No.: PCT/EP2009/064881
§ 371 (c)(1),
(2), (4) Date: May 9, 2011

(87) PCT Pub. No.: WO2010/052329
PCT Pub. Date: May 14, 2010

(65) Prior Publication Data
US 2011/0218245 A1 Sep. 8, 2011

(30) Foreign Application Priority Data
Nov. 10, 2008 (IT) .............................. MI2008A1982

(51) Int. Cl.
| A61K 31/202 | (2006.01) |
| C07C 57/03 | (2006.01) |
| C07C 33/02 | (2006.01) |
| A61K 31/045 | (2006.01) |
| A61K 31/11 | (2006.01) |
| A61K 31/22 | (2006.01) |
| A61K 31/231 | (2006.01) |
| A61K 31/232 | (2006.01) |

(52) U.S. Cl.
CPC ............ A61K 31/11 (2013.01); A61K 31/045 (2013.01); A61K 31/22 (2013.01); A61K 31/231 (2013.01); A61K 31/232 (2013.01)

(58) Field of Classification Search
USPC ....................................................... 514/552
See application file for complete search history.

(56) References Cited

U.S. PATENT DOCUMENTS 4,898,885 A 2/1990 Horrobin
2003/0129268 A1 7/2003 Msika et al.

FOREIGN PATENT DOCUMENTS

JP 2008-88127 4/2008
WO WO 03095403 11/2003

OTHER PUBLICATIONS

Mukherjee, Cardioprotection with the Parrodiene 2,4,6-Octatrienal and Its Potassium Salt through Activation of the Akt-Bcl-2 Survival Pathway, Mar. 27, 2009, J. Nat. Prod., 72, pp. 871-875.*
Berge, Pharmaceutical Salts, Journal of Pharmaceutical Sciences, 1977, 66, pp. 1-19.*
Shimo, Mitsuo. et al, "Studies on Search of New Antimicrobial Active Compound for Food Preservation" Journal of Food Hygienics, 1996, vol. 7, No. 1, p. 55-59 (with English Abstract).
Niederpruem, H-J. et al, 1995, "Inhibition of Steroid 5α-Reductase Activity by Aliphatic Fatty Acids," *Annals of the New York Academy of Sciences*, 768:227-230.
Liang T. 1991, "Inhibition of Steroid 5α-Reductase Activity by Aliphatic Fatty Acids," *Clinical Research*, 39(3): P720A.
Liang T. 1992, "Inhibition of Steroid 5α-Reductase Activity by Specific Aliphatic Unsaturated Fatty Acids," *Biochemical Journal*, 285: 557-562.
Pine E et al. "Biological activity of parrodienes, a new class of polyunsaturated linear aldehydes similar to carotenoids" Drugs Under Experimental and Clinical Research, Bioscience Ediprint Inc., XX, vol. 30, No. 5-6, Jan. 1, 2004 (Jan. 1, 2004), pp. 203-206, XP008110867 ISSN: 0378-6501 (the whole document).
Bissett D L et al. "Protective effect of topically applied conjugated hexadienes against ultraviolet radiation-induced chronic skin damage in the hairless mouse" Photodermatology, Photoimmunology & Photomedicine, Blackwell Publishing, vol. 7, No. 2, Apr. 1, 1990 (Apr. 1, 1990), pp. 63-67, XP008110449 ISSN: 0905-4383 (the whole document).
Lee Ping C. et al. "Short term feeding of hexadienal to postnatal rats: Effects on stomach aldehyde dehydrogenase" Biosis Host—Biosis, Jan. 13, 2003 (Jan. 13, 2003), XP002248781 (the whole document).

(Continued)

*Primary Examiner* — San-Ming Hui
*Assistant Examiner* — Andrew Lee
(74) *Attorney, Agent, or Firm* — Stephanie X. Wang; DLA Piper LLP (US)

(57) ABSTRACT

The object of the present invention is the use of compounds designed to inhibit the activity of the enzyme 5α-reductase. This is a novel use of compounds of general formula (I):

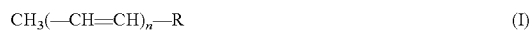

$$CH_3\text{---}(CH\text{=}CH)_n\text{---}R \qquad (I)$$

where n=from 2 to 7, and
R is chosen from among: CHO, $CH_2OH$, $CH_2O\text{---}CO\text{---}R'$, $CO\text{---}O^{(-)}$,
where R' is chosen from among H, and the alky from $C_1$ to $C_{22}$,
each compound of general formula (I) being used as such or in mixtures with other compounds,
as the active principle in a pharmaceutical or cosmetic composition designed to inhibit the action of the enzyme 5α-reductase, and of the pharmaceutical or cosmetic compositions deriving therefrom.

14 Claims, No Drawings

(56) References Cited

OTHER PUBLICATIONS

Rigano L et al. "Novel retinol-like actives from parrots feathers" IFSCC Magazine, Allured Pub., Carol Stream, IL, US, vol. 11, No. 4, Oct. 6, 2008, pp. 323-330, XP008110401 ISSN: 1520-4561 figures 3, 4, 11, 13-18 p. 325, middle column, paragraph 3, p. 329, right-hand column, paragraph 2.

* cited by examiner

USE OF COMPOUNDS TO INHIBIT 5 α-REDUCTASE ENZYME ACTIVITY, AND PHARMACEUTICAL AND COSMETIC COMPOSTIONS CONTAINING THEM

FIELD OF THE INVENTION

The object of the present invention is the use of compounds designed to inhibit the activity of the enzyme 5α-reductase.

PRIOR ART

There are ample reports in the literature on the activity of 5α-reductase, an enzyme contained in the skin, melanocytes, fibroblasts and keratinocytes, that convert testosterone into dihydrotestosterone (DHT), a hormone that has a key role in numerous skin disorders, including acne vulgaris, hirsutism, seborrhoea and alopecia. The following references on the topic are worth mentioning:

Baxendale, P. M. et al, (1983) Clinical Endocrinology, 18:447.
Bayne E. K., Flanagan J., Instein M., Ayala J., Chang B., Azzolina B., Whiting D. A., Mumford R. A., Thiboutot D., Singer I. I., Harris G. (1999). Immunohistochemical localization of types 1 and 2 5-alpha reductase in human scalp. Br J Dermatol Seo; 141(3): 481-91.
Bernard, F.-X., Barrault, C., Deguercy, A., De Wever, B. and Rosdy, M. (2002). Expression of type 1 5α-reductase and metabolism of testosterone in reconstructed human epidermis (SkinEthic®): a new model for screening skin-targeted androgen modulators. Int. J. Cosmet. Sci., 22(6): 397.
Colin W. Bayne, Frank Donnelly, Margaret Ross, Fouad K. Habib. (1999). "*Serenoa repens* (Permixon): a 5alpha-reductase types I and II inhibitor: new evidence in a coculture model of BPH." Prostate 40(4): 232-41.
Délos S., Carsol J. L., Ghazarossian E., Raynaud J. P., Martin P. M. (1\995). Testosterone metabolism in primary cultures of human prostate epithelial cells and fibroblasts. J Steroid Biochem Mol Biol, 55(3-4): 375-83.
Gomella Leonard, G. (2005). Chemoprevention using dutasteride: the REDUCE trial. Curr. Opin. Urol., 15(1):29-32.
Iehlé C., Délos S., Guirou O., Tate R., Raynaud J. P., Martin P M. (1995). Human prostatic steroid 5 alpha-reductase isoforms—a comparative study of selective inhibitors. J Steroid Biochem Mol Biol, 54:(5-6): 273-9.
J. Clin. Periodontol., 25(1):67.
Prager N., Bickett K., French N., Marcovici G. A. (2002). Randomized, double-blind, placebo-controlled trial to determine the effectiveness of botanically derived inhibitors of 5-alpha-reductase in the treatment of androgenetic alopecia. J Altern Complement Med., 8(2):143-52.
Rittmaster, R. S. (1994). Finasteride. N. Engl. J. Med., 330:120-125.
Santner S. J., Albertson B., Zhang G. Y., Zhang G. H., Santulli M., Wang C., Deners L. M., Shackleton, Santen R. J. (1998). Comparative rates of androgen production and metabolism in Caucasian and Chinese subjects. J Clin Endocrinol Metab, 83(6):2104-9.
Soory, M. and Virdi., H. (1998). Effects of the anti-androgen finasteride on 5α-reductase activity in human gingival fibroblasts in response to minocycline.

SUMMARY OF THE INVENTION

The object of the present invention is the use of compounds designed to inhibit the activity of the enzyme 5α-reductase. This involves the novel use of the compounds of general formula (I):

$$CH_3(-CH=CH)_n-R \quad (I)$$

where n=from 2 to 7, and
R is chosen from among: CHO, $CH_2OH$, $CH_2O-CO-R'$, $CO-O^{(-)}$,
where R' is chosen from among H, the alkyl from $C_1$ to $C_{22}$, each compound of general formula (I), being used as such or in mixtures with other compounds,
as an active principle in a pharmaceutical or cosmetic composition designed to inhibit the action of the enzyme 5α-reductase.

Another object of the invention concerns the pharmaceutical and cosmetic compositions deriving therefrom.

DETAILED DESCRIPTION OF THE INVENTION

An experimental study, reported below as part of the present description, has surprisingly demonstrated that the enzyme 5α-reductase can be strongly inhibited in vitro in a cell line of mouse fibroblasts when said compounds according to the invention are used.

The invention thus refers to the use of the compounds (I) formulated as active principles for any therapeutic or cosmetic application in which said inhibition of the enzyme 5α-reductase produces an advantageous effect. In particular, this refers to the following applications in humans:
  for treating all forms of alopecia
  for promoting hair regrowth
  for promoting seboregulation
  for promoting skin integrity by increasing the collagen and reinforcing the elastin
  for acne treatment
  for treating prostatic disorders, be it prostate cancer or benign prostatic hypertrophy.

Another object of the present invention is a composition for the above use and indications for therapeutic as well as cosmetic purposes, that comprises said active principle, for both topical and systemic administration, e.g. for oral use.

A composition according to the invention preferably comprises said active principle in quantities coming within the range of 0.05-0.3% w/w of the composition. Preferred compounds (I) formulated according to the present invention are as follows:
2,4,6-octatrien-1-ol
2,4,6-octatrienoic acid
2,4,6-octatrienoic acid sodium salt
2,4,6-octatrienoic acid L-lysine salt
2,4,6-octatrien-1-ol palmitate
2,4,6-octatrien-al The following examples illustrate the invention without limiting its scope in any way.

Characterisation data and formulas of some of the compounds of general formula (I) are given below.

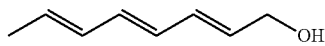

$C_8H_{12}O$ mw 124.18
2E,4E,6E-Octatrien-1-ol
CAS #: 130971-00-5

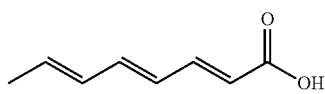

$C_8H_{10}O_2$ mw 138.17
2E,4E,6E-Octa-2,4,6-trienoic acid
CAS #: 5205-32-3

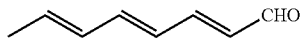

$C_8H_{10}O$ mw 122.17
2,4,6-Octatrienal (E,E,E), all-trans-2,4,6-Octatrienal
CAS #: 16326-86-6

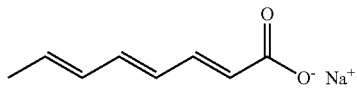

$C_8H_9O_2 \cdot Na$ mw 160.15
2E,4E,6E-Octa-2,4,6-trienoic acid sodium salt
CAS #: not available

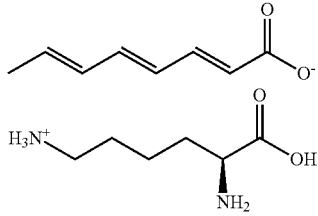

$C_8H_9O_2 \cdot C_6H_{15}N_2O_2$ mw 284.36
2E,4E,6E-Octa-2,4,6-trienoic acid L-lysine salt
CAS #: not available

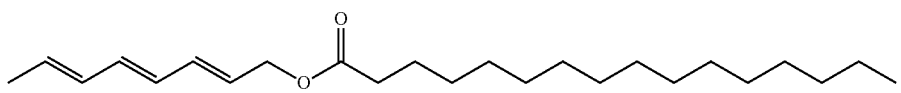 [SMILES: C/C=C/C=C/C=C/COC(=O)CCCCCCCCCCCCCCC]

$C_{24}H_{42}O_2$ mw 362.60
2E,4E,6E-Octatrien-1-ol, palmitate
CAS #: not available Non-limiting examples of composition particularly suitable for the above-stated use are given below.

The quantities of the components, identified according to the INCI nomenclature, are expressed as weight/weight percentages:

Example 1

Liposomal Acne Gel

| INCI name | w/w % |
| --- | --- |
| Aristoflex | 0.1-0.5 |
| Phosal 75 SA | 2.0-4.0 |
| 2,4,6-octatrienoic acid | 0.05-0.3 |
| Labrasol | 1-3 |
| Nipaguard | 0.8-1.2 |
| Lactic acid | q.s. pH 5 |
| Water q.s. | 100 |

Example 2

Liposomal Hair Loss Gel

| INCI name | w/w % |
| --- | --- |
| Aristoflex | 0.1-0.5 |
| Phosal 75 SA | 2.0-4.0 |
| 2,4,6-octatrien-1-ol | 0.05-0.3 |
| Labrasol | 1-3 |
| Nipaguard | 0.8-1.2 |
| Lactic acid | q.s. pH 5 |
| Water q.s. | 100 |

Example 3

Hair Loss Shampoo

| INCI name | w/w % |
| --- | --- |
| EDTA 4Na | 0.2 |
| Polymer JR 400 | 0.2-0.6 |
| REWOMID IPP 240 | 0.8-1.2 |
| REWODERM LI S 80 | 3 |
| Water | 16.68 |
| PROTELAN LS 9011 | 9 |
| 2,4,6-octatrienoic acid | 0.002-0.3 |
| NATURAL EXTRACT AP | 0.2-0.6 |
| PANTENOL | 0.2 |
| ZETESOL MGS | 20.4 |

-continued

| INCI name | w/w % |
| --- | --- |
| PROTELAN AG11 | 0.5-1.5 |
| WATER | 2 |
| ROSEMARY dry extract | 0.06 |
| BC2262 | 0.5 |
| BC2211 | 0.8 |
| Soligel | 0.1-1 |
| AQUAFLEX | 1 |
| PERFUME | 0.6 |
| BHA | 0.01 |
| CROSILK LIQUID | 0.5-1 |
| GLUCQUAT 100 | 0.5 |
| DRAGODERM | 1 |
| HAIRESPHERES BIOGENIN | 0.25 |
| MIRASHEEN CP 820 | 4 |
| NIPAGUARD SMG | 0.8 |
| CITRIC ACID | 0.6 |
| WATER q.s. | 100 |

Example 4

Hair Loss Shampoo

| INCI name | w/w % |
| --- | --- |
| EDTA 4Na | 0.2 |
| POLYMER JR 400 | 0.2-0.6 |
| REWOMID IPP 240 | 0.8-1.2 |
| REWODERM LI S 80 | 3 |
| WATER | 16.68 |
| PROTELAN LS 9011 | 9 |
| 2,4,6-octatrien-1-ol | 0.002-0.3 |
| NATURAL EXTRACT AP | 0.2-0.6 |
| PANTENOL | 0.2 |
| ZETESOL MGS | 20.4 |
| PROTELAN AG11 | 0.5-1.5 |
| WATER | 2 |
| ROSEMARY dry extract | 0.06 |
| BC2262 | 0.5 |
| BC2211 | 0.8 |
| Soligel | 0.1-1 |
| AQUAFLEX | 1 |
| PERFUME | 0.6 |
| BHA | 0.01 |
| CROSILK LIQUID | 0.5-1 |
| GLUCQUAT 100 | 0.5 |
| DRAGODERM | 1 |
| HAIRESPHERES BIOGENIN | 0.25 |
| MIRASHEEN CP 820 | 4 |
| NIPAGUARD SMG | 0.8 |
| CITRIC ACID | 0.6 |
| WATER q.s. | 100 |

Example 5

Hair Loss Mousse Lotion

| INCI name | w/w % |
| --- | --- |
| Calcium pantothenate | 0.390 |
| 2,4,6-octatrien-1-ol | 0.05-0.3 |
| Biotin | 0.004 |
| Spermidine HCl | 0.01-0.1 |
| Disodium EDTA | 0.060 |
| Ajuga reptans leaf extract | 0.01-0.1 |
| Taurine | 2.000 |
| Glycerine | 0.80-4 |
| Tocopherols | 0.02-0.20 |
| Vitis vinifera grape seed extract | 0.02-0.10 |
| Alcohol | 11-15 |
| Polyquaternium 16 | 0.05-0.20 |
| PEG-40 hydrogenated castor oil | 0.50-4 |
| Perfume | 0.500 |
| Sodium olivamphoacetate | 0.80-3 |
| Water q.s. | 100 |

Experimental Study: In Vitro Assessment of the Modulation of 5α-Reductase Activity on Mouse Fibroblasts Compounds Studied 2,4,6 octatrien-1-ol according to the invention, compared with:
  alternative *Boehmeria*
  traditional *Boehmeria*
  *Ajuga reptans* extract
  Finasteride Tests Performed Assessment of the modulation of 5α-reductase activity after treatment for 48 hours with the above-stated compounds in a cell line of mouse fibroblasts.

Description of the Study

Aim

For this test, the fibroblasts were pretreated with testosterone to increase the basal production of 5α-reductase, then they were treated with the above-mentioned compounds for 48 hours.

At the end of the treatment, the conversion of testosterone into DHT was measured in the treated and untreated cell cultures, using a two-way ELISA. This procedure enables an estimation of the percentage inhibition or stimulation of the specific activity of 5α-reductase.

As a positive control, we used a titrated extract of *Serenoa repens* (saw palmetto), a plant known in the pharmacopoeia for its capacity to inhibit 5α-reductase and recommended for said purpose in the treatment of prostatic hyperplasia in males.

Description of the Samples

| Samples | Appearance |
| --- | --- |
| 2,4,6-octatrien-1-ol | dark yellow powder |
| alternative Boehmeria | brown powder |
| traditional Boehmeria | brown powder |
| Ajuga reptans extract | dark yellow powder |
| Finasteride | white powder |

Experimental Model

The cell model used for the in vitro test consisted of mouse fibroblasts Balb/c-3T3. This cell line derives from fibroblasts of Swiss albino mouse embryos.

Sample Preparation

The samples of the above-described compounds were solubilised as follows:
  2,4,6-octatrien-1-ol: 1 mg/ml in absolute ethanol
  alternative *Boehmeria*: 5 mg/ml in growth medium+5% DMSO
  traditional *Boehmeria*: 2.5 mg/ml in growth medium+5% DMSO
  *Ajuga reptans* extract: 5 mg/ml in growth medium+5% DMSO
  Finasteride: 5 mg/ml in absolute ethanol
  *Serenoa repens*: 10 µl/ml in absolute ethanol Treatment and Exposure Pre-Incubation The cells were seeded in 25 cm² flasks (T25) in DMEM (Dulbecco's Minimum Essential Medium) with the addition of 10% FBS (foetal bovine serum). As soon as confluence was achieved, the cultures were treated for 24 hours with 10 ng/ml of testosterone.

Treatment

After the pre-incubation phase, the cell cultures were treated with said samples at the final concentration of 0.1 mg/ml. The *Serenoa repens* extract at 0.1 mg/ml was used as a positive control, while the negative control consisted in plates treated with the solvent. Exposure was protracted for 48 hours in the incubator at 37° C., 5% $CO_2$, renewing the medium every 24 hours. Each sample was tested in duplicate.

At the end of the experiment, a cell count was conducted to assess any cytotoxic effects. The of DHT and testosterone content was measured using immunodiagnostic tests (ELISA) in the extracellular (conditioned growth media) and in the intracellular (cell extracts) compartments.

Cell Extract Composition

At the end of the experiment, the growth medium was collected from each flask and a cell extract was prepared.

This was done in four stages:
trypsinisation of the cell layer in situ in the flask
centrifugation and collection of the cells in pellets
extraction with Triton X-100 (1% in basal medium)
ultrasonication for 30 minutes.

DHT and Testosterone Measurement

The two hormones, DHT and testosterone, were measured both in the supernatant (extracellular DHT/testosterone) and in the cell extracts (intracellular DHT/testosterone).

In developing the 5α-reductase test, we were able to establish that the testosterone interferes with the DHT measurement (crosslinking) for the amount of 8.7%, whatever the concentration of either of the hormones. It is therefore of fundamental importance to determine the quantity of testosterone remaining at the end of the test in order to distinguish it from the newly-synthesised DHT. Moreover, the presence of DHT in foetal bovine serum (FBS), the main component in the growth medium, represents a source of exogenous DHT that must be taken into account in calculating the DHT actually produced by the cells starting from the testosterone.

The method involves the composition of a standard curve, calculated in an appropriate range of concentrations, and uses specific antibodies immobilised on a solid substrate directed against DHT/testosterone, and a reagent that competes for binding to the antibody.

The reaction is detected by means of a substrate solution and develops a compound with a colouring inversely proportional to the concentration of the DHT/testosterone content. For each sample, the absorbance is read at 450 nm. The final calculation of the DHT includes subtracting the interference of the testosterone and of the exogenous DHT contributed by the FBS in the growth medium.

Results
Testosterone Assay

| Sample | Testosterone - ng/ml | |
|---|---|---|
| | supernatant | cell extract |
| Control | 0 | 1 |
| Serenoa 10 μg/ml | 1.5 | 3.5 |
| Serenoa 100 μg/ml | 0 | 1.75 |
| 2,4,6-octatrien-1-ol 100 μg/ml | 1.25 | 1 |
| alternative Boehmeria 100 μg/ml | 0 | 5.5 |
| traditional Boehmeria 100 μg/ml | 0 | 0.5 |
| Ajuga reptans 100 μg/ml | 0 | 3.75 |
| Finasteride 100 μg/ml | 0 | 3.1 |

Dihydro-Testosterone (DHT) Assay

| Sample | DHT - pg/ml | |
|---|---|---|
| | supernatant | cell extract |
| Control | 450 | 300 |
| Serenoa 10 μg/ml | 400 | 650 |
| Serenoa 100 μg/ml | 275 | 175 |
| 2,4,6-octatrien-1-ol 100 μg/ml | 425 | 450 |
| alternative Boehmeria 100 μg/ml | 425 | 625 |
| traditional Boehmeria 100 μg/ml | 300 | 425 |
| Ajuga reptans 100 μg/ml | 275 | 425 |
| Finasteride 100 μg/ml | 450 | 400 |

Final Dihydro-Testosterone (DHT) Determination

As stated above, the real concentration of DHT is deduced according to the formula:

[measured DHT]−[bovine serum DHT]−[testosterone crosslinking]

The quantity of DHT contained in the growth medium (coming from the bovine serum) is:
0.1 ng/ml The testosterone crosslinking is calculated according to the formula:

[testosterone concentration]×8.7/100

| | Final DHT - pg/ml | |
|---|---|---|
| Sample | supernatant | cell extract |
| Control | 350 | 213 |
| Serenoa 10 μg/ml | 170 | 346 |
| Serenoa 100 μg/ml | 169 | 23 |
| 2,4,6-octatrien-1-ol 100 μg/ml | 216 | 363 |
| alternative B. 100 μg/ml | 325 | 147 |
| traditional B. 100 μg/ml | 200 | 382 |
| Ajuga reptans 100 μg/ml | 175 | 99 |
| Finasteride 100 μg/ml | 350 | 130 |

Since the volume of the supernatant is known to be 10 ml and the volume of the cell extract is 0.5 ml, the total quantity of DHT produced per flask of cell culture can be calculated.

| Sample | Total DHT produced (ng) |
|---|---|
| Control | 3.61 |
| Serenoa 10 μg/ml | 1.87 |
| Serenoa 100 μg/ml | 1.70 |
| 2,4,6-octatrien-1-ol 100 μg/ml | 2.34 |
| alternative B. 100 μg/ml | 3.32 |
| traditional B. 100 μg/ml | 2.19 |
| Ajuga reptans 100 μg/ml | 1.80 |
| Finasteride 100 μg/ml | 3.57 |

Then the percentage 5α-reductase inhibition can be calculated. The result is expressed as the mean of the experimental measurements. The overall experimental error is estimated to be no higher than 10%. Integrating this variability in the various calculations, enables an estimation of the confidence interval that is expressed as ±0.x in the following final table.

| | | 48 hours | |
|---|---|---|---|
| | | Total DHT ng (±SE) | % inhibition |
| Pre-incubation for 24 hours with testosterone 10 ng/ml | Negative control | 3.6 (±0.3) | — |
| | Positive control Serenoa repens 0.1 mg/ml | 1.7 (±0.1) | 46-49 |
| | 2,4,6-octatrien-1-ol 0.1 mg/ml | 2.3 (±0.1) | 27-43 |
| | alternative Boehmeria 0.1 mg/ml | 3.3 (±0.2) | 0-21 |
| | traditional Boehmeria 0.1 mg/ml | 2.2 (±0.2) | 27-48 |
| | Ajuga reptans extract 0.1 mg/ml | 0.5 (±0.0) | 85-87 |
| | Finasteride 0.1 mg/ml | 3.6 (±0.3) | 0-15* |

*The confidence interval for finasteride would be ±−18-15; given that the percentage inhibition cannot be negative, the result is expressed assuming 0 as the lower limit.

Comments

These results demonstrate that four of the above-defined compounds are capable of significantly inhibiting the enzyme 5α-reductase, i.e. 2,4,6-octatrien-1-ol, traditional *Boehmeria*, *Ajuga reptans* extract and alternative *Boehmeria*).

In particular, *Ajuga reptans* extract had a stronger inhibiting effect (85-87%) than the positive control *Serenoa repens* (46-49%), while the inhibition induced by 2,4,6-octatrien-1-ol and traditional *Boehmeria* was approximately 27-48%.

The least active substance was the alternative *Boehmeria*.

In the experimental conditions described, finasteride, known in the literature as an inhibitor of 5α-reductase, was found to have no real inhibitory effect. This finding can be explained by the fact that 5α-reductase exists in two isoforms that are expressed differently depending on the tissues involved: type 1 is predominant in the skin, while type 2 is found mainly in the prostate. Moreover, finasteride is known to preferentially inhibit the isoenzyme 5α-reductase type 2, and to have a limited effect on type 1 (Rittmaster, 1994; Soory and Virdi, 1998; Bernard et al., 2002; Gomella Leonard, 2005). It is consequently hardly surprising that finasteride failed to significantly inhibit the 5α-reductase in the above-mentioned model of cell cultures.

*Serenoa repens* extract inhibits both the enzymes, type 1 and type 2, as confirmed by the present experiment. Similar results were reported by Prager (2002), who found a stronger inhibition after treatment with *Serenoa repens* than after finasteride: in Prager's model, the inhibition induced by *Serenoa repens* was 50-60%, as in the present study. Data reported by Iehle et al (1995) confirmed these results.

Conclusions

In the above-described experimental study, the compounds 2,4,6-octatrien-1-ol according to the present invention, traditional *Boehmeria*, and *Ajuga reptans* extract all inhibited the activity in vitro of 5α-reductase significantly by comparison with an untreated control.

The alternative *Boehmeria* only slightly inhibited 5α-reductase activity in vitro (<10%) by comparison with the untreated control.

Finasteride showed no significant inhibitory effect.

Clinical Study: Treatment of Androgenetic Alopecia and Alopecia Greata

A clinical pilot study was also conducted to assess the efficacy of a composition according to the invention in the treatment of male and female androgenetic alopecia and alopecia greata.

In the composition according to the invention forming the object of this clinical study, said active principle was a salt, and a potassium salt in particular, of 2,4,6-octatrienoic acid, formulated for topical administration on the scalp, in a single daily dose.

Materials and Methods

Group 1: Androgenetic Alopecia

Thirty individuals of both genders were recruited (15 males and 15 females) aged between 18 and 55 years, suffering from androgenetic alopecia (grades I-III according to the Hamilton scale for men, and I-II according to the Ludwig scale for women). Since this was a pilot study, an open trial was conducted, administering the composition of the invention.

Exclusion criteria from the study were as follows:
concomitant hormonal and/or pharmacological therapies;
pregnancy and breast-feeding;
systemic hormonal, metabolic and autoimmune diseases;
specific trichological treatments in the previous three months;
concomitant inflammatory diseases of the scalp, e.g. seborrhoeic dermatitis, irritative or allergic dermatitis.

The clinical and dermoscopic assessment of the individuals to treat focused on: hair shaft diameter, presence of a perifollicular halo, evaluation of the anagen phase by epiluminescence study of the bulb.

After the baseline assessment at $T_0$, before starting the treatment, two evaluations after the treatment were conducted, one at $T_1$ after 1 month, and one at $T_2$ after 3 months.

Results

Hair Shaft Diameter

At each follow-up assessment, a clinical evaluation was performed using epiluminescence to establish the hair shaft diameter in a previously-established and marked area (Mole-Max II, Dermal Instruments Italia).

The increase in hair shaft diameter was judged as follows:
A) highly significant in 62% of cases;
B) significant in 21%;
C) not significant in 17%.

This percentage of improvement increased from T1 to T2.

In particular, the results indicated that the mean hair shaft diameter at T0 was 0.4 mm in all individuals.

At T2, the above-mentioned Group A) had a hair shaft diameter of 0.7 mm.

In Group B) the hair shaft diameter was 0.6 mm at T2.

Group C) had a hair shaft diameter of 0.4 mm at T2.

Percentage of Bulbs in the Anagen Phase

The percentage of bulbs in the anagen phase at T0 was a mean 56% for all the individuals considered.

At T2 it had changed as follows:
A) 83%
B) 74%
C) 61%

2) Group with Alopecia Greata

Alopecia greata (also called area celsi) is a disease involving sudden hair loss typically giving rise to bald patches (or areas).

A significant characteristic of the evolutional stages of alopecia greata is the presence of "exclamation mark" hairs, so called because they appear tapered towards the base.

For the group of individuals treated, the pilot study only enabled us to identify a trend (clinical improvement, stability, worsening) within the short time span considered, i.e. from the baseline $T_0$ before starting the treatment up to $T_2$ after three months of treatment, based on the following parameters:

hair loss
progression of bald patches on the scalp
presence of exclamation mark hairs Results Hair loss: The defluvium of hair in the areas affected by the alopecia greata diminished in 55% of the individuals with active androgenetic alopecia.

Progression of bald patches: There was evidence of a stoppage in the progression and a slight reduction in the extent of the bald patches on the scalp in 43% of the individuals, and of a stabilisation of the patches in 15%.

Presence of exclamation mark hairs: The number of exclamation mark hairs changed from a mean 82% at T0 to 46% at T2 in the individuals with a stabilisation or slight improvement in their bald patches, and from a mean 83% at T0 to a mean 82% in the individuals with worsening bald patches.

Conclusions

This clinical study demonstrated that the topical administration on the scalp of a composition according to the invention (active principle: potassium salt of 2,4,6-octatrienoic acid) has an effective action on the bulbs of hair suffering from androgenetic alopecia and area celsi as follows:

Androgenetic alopecia group. The fundamental and pathognomonic parameters for androgenetic alopecia were modified in a globally positive manner in 83% of the individuals treated. Both the hair shaft diameter and the percentage of bulbs in the anagen phase increased significantly in the individuals responding to the treatment. None of the individuals showed any side effects after using the product.

Alopecia greata group. From the pilot study it emerged that a global trend towards an improvement was reported in 58% of the individuals treated (clinical improvement and stabilisation of the bald patches).

The number of exclamation mark hairs (a pathognomonic sign of area celsi) was significantly reduced in the individuals who tended to improve after the treatment, and remained unchanged in the individuals who failed to respond to the treatment. None of the individuals revealed any side effects after using the product.

Further Indication

Moreover, data obtained in a further clinical study showed that topical treatment of the scalp with a composition according to the invention is promising for the prevention of premature apoptosis and catagen in transplanted hair follicles following hair transplantation on the scalp (active principle: 2,4,6-octatrienoic acid salt, once a day from 15 days before to 90 days after the transplant).

On the whole, based on the above description, it was concluded that the compounds according to the invention demonstrate that they achieve the initially stated object as well as further advantages.

The invention claimed is:

1. A topical pharmaceutical or cosmetic composition to inhibit the action of the enzyme 5α-reductase in humans, comprising as active principle a compound having general formula (I):

$$CH_3(-CH=CH)_n-R \qquad (I)$$

wherein n=3-7,

R is selected among: $CH_2O-CO-R'$, $CO-OH$, $CO-O^{(-)}$, wherein R' is selected among H, alkyl from $C_1$ to $C_{22}$, each compound of general formula (I) being used as such or in a mixture thereof, with any suitable excipient for a topical administration onto the skin or the scalp.

2. The composition according to claim 1 to treat alopecia.

3. The composition according to claim 1 to promote hair growth.

4. The composition according to claim 1 to promote regulation of sebum on the human scalp.

5. The composition according to claim 1 to promote skin integrity by improving collagen and elastin robustness.

6. The composition according to claim 1 to treat acne.

7. The composition according to claim 1 to treat prostatic diseases, namely prostate cancer and benign prostatic hyperplasia.

8. The composition according to claim 1, wherein the active principle is 2,4,6-octatrienoic acid.

9. The composition according to claim 1, wherein the active principle is a compound having general formula (I) wherein R is $CO-O^{(-)}$.

10. The composition according to claim 9, wherein the active principle is a salt of 2,4,6-octatrienoic acid.

11. The composition according to claim 9, wherein the active principle is 2,4,6-octatrienoic acid sodium salt.

12. The composition according to claim 9, wherein the active principle is 2,4,6-octatrienoic acid L-lysine salt.

13. The composition according to claim 1, wherein the active principle is a mixture of two or more of the compounds of formula (I).

14. The composition according to claim 1, comprising an amount of the active principle in the range 0.05-0.3% by weight.

* * * * *